(12) United States Patent
Betkoski et al.

(10) Patent No.: US 8,470,883 B2
(45) Date of Patent: Jun. 25, 2013

(54) PRESERVATIVE SYSTEM AND COMPOSITION BASED ON GLYCINATE AND HYDROXYETHYL SULFONATE SALT COMBINATION

(75) Inventors: Roberta Marie Betkoski, Seymour, CT (US); Deidre Lee Mitchell, Oxford, CT (US); Kavssery Parameswaran Ananthapadmanabhan, Woodbury, CT (US); Lin Yang, Woodbridge, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 330 days.

(21) Appl. No.: 12/834,074

(22) Filed: Jul. 12, 2010

(65) Prior Publication Data

US 2012/0009128 A1    Jan. 12, 2012

(51) Int. Cl.
 *A01N 37/12*    (2006.01)
 *A01N 37/44*    (2006.01)
 *A61K 31/195*    (2006.01)

(52) U.S. Cl.
 USPC .......................................... 514/561

(58) Field of Classification Search
 None
 See application file for complete search history.

(56) References Cited

U.S. PATENT DOCUMENTS

| | | | |
|---|---|---|---|
| 6,034,043 A * | 3/2000 | Fujiwara et al. | 510/130 |
| 7,282,471 B2 | 10/2007 | Harichian et al. | |
| 7,659,233 B2 | 2/2010 | Hurley et al. | |
| 2006/0019844 A1 * | 1/2006 | Aubrun-Sonneville et al. | 510/127 |
| 2007/0280976 A1 | 12/2007 | Taylor | |
| 2008/0196168 A1 * | 8/2008 | Schubert et al. | 8/94.21 |

FOREIGN PATENT DOCUMENTS

| | | | |
|---|---|---|---|
| JP | 1233264 | | 9/1989 |
| JP | 2006273816 | | 10/2006 |
| JP | 2006273816 A | * | 10/2006 |
| WO | WO9635410 | | 2/2006 |
| WO | WO2006026875 A1 | | 3/2006 |
| WO | WO2009071776 A2 | | 6/2009 |
| ZA | 7103553 | | 2/1972 |

OTHER PUBLICATIONS

Co-pending application—Applicant: Dasgupta et al.; Filed Jul. 12, 2010; Entitled: Foam Enhancement of Fatty Acyl Glycinate Surfactants.

Co-pending application—Applicant: Mitchell et al.; Filed Jul. 12, 2010; Entitled: Preservative System and Composition based on Glycinate and Dihydroxypropyl Quaternary Ammonium Salt Combination.

Mamada et al., Antimicrobial Characteristics and Adsorption to Halogenated Glycerine, Bokin Bobai Abstract, 1989, vol. 17, No. 9, 413-418.

* cited by examiner

*Primary Examiner* — Sue Liu
*Assistant Examiner* — Thor Nielsen
(74) *Attorney, Agent, or Firm* — Karen E. Klumas

(57) ABSTRACT

A preservative system and a personal care composition containing that system is provided which includes the preservative combination of a $C_{10}$-$C_{24}$ acyl glycinate salt and a hydroxyethyl sulfonate salt. This preservative system is effective against gram negative bacteria, particularly *Pseudomonas aeruginosa*.

10 Claims, No Drawings

PRESERVATIVE SYSTEM AND COMPOSITION BASED ON GLYCINATE AND HYDROXYETHYL SULFONATE SALT COMBINATION

BACKGROUND OF THE INVENTION

1. Field of the Invention

The invention concerns an anti-bacterial active mixture and use in personal care products.

2. The Related Art

Water containing formulations are prone to experience bacterial contamination. Preservatives are vitally necessary in defending against micro organisms. Gram negative bacilli such as *Pseudomonas aeruginosa* are particularly nasty organisms. Indeed, the U.S. Federal Drug Administration classifies *Pseudomonas aeruginosa* as an "objectionable organism". Medically this bacteria is a significant human pathogen.

Formulations intended for pharmaceutical and personal care compositions are highly affected by the problem.

Part of the issue involves ability of the micro organism to mutate. New preservatives must continually be developed to fight the contamination. Consequently, there is a need for new preservative systems that can meet the challenge of gram negative bacteria, and most especially of *Pseudomonas aeruginosa*.

SUMMARY OF THE INVENTION

A preservative system is provided which includes:
(i) a $C_{10}$-$C_{24}$ acyl glycinate salt of formula (I)

wherein R is a $C_9$-$C_{23}$ alkyl group, and X is a cation selected from the group consisting of sodium, potassium, ammonium and triethanolammonium ions; and
(ii) a salt of hydroxyethyl sulfonate of formula (II)

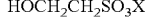

wherein X is a cation selected from the group consisting of sodium, potassium, ammonium and triethanolammonium ions.

Further provided is a personal care composition which includes:
(i) from about 0.1 to about 20% of a $C_{10}$-$C_{24}$ acyl glycinate salt of formula (I)

wherein R is a $C_9$-$C_{23}$ alkyl group, and X is a cation selected from the group consisting of sodium, potassium, ammonium and triethanolammonium ions;
(ii) from about 0.1 to about 10% of a salt of hydroxyethyl sulfonate of formula (II)

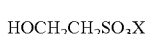

wherein X is a cation selected from the group consisting of sodium, potassium, ammonium and triethanolammonium ions; and
(iii) water.

DETAILED DESCRIPTION OF THE INVENTION

Now it has been found that gram negative bacteria, especially *Pseudomonas aeruginosa*, can be killed by a combination of a $C_{10}$-$C_{24}$ acyl glycinate salt and a hydroxyethyl sulfonate salt. The combination in a personal care composition can reduce the amount of *Pseudomonas aeruginosa* by a Log Reduction of at least 2, preferably at least 3.5 and optimally at least 5 within 48 hours of application to an aqueous system.

Accordingly, a first element of the present invention is that of a $C_{10}$-$C_{24}$ acyl glycinate salt. These salts are represented by the formula (I)

wherein R is a $C_9$-$C_{23}$ alkyl group, and X is a cation selected from the group consisting of sodium, potassium, ammonium and triethanolammonium ions.

For the preservative system the ratio by weight of the glycinate and hydroxyethyl sulfonate salts may respectively range from about 200:1 to about 1:5, preferably from about 150:1 to about 1:1, optimally from about 100:1 to about 1:1.

In personal care compositions the amounts of the glycinate salt may range from about 0.1 to about 20%, preferably from about 1 to about 15%, and optimally from about 3 to about 8% by weight of the composition. Most preferred among the glycinate salts is cocoyl glycinate salt, more particularly sodium cocoyl glycinate.

A second element of the present invention is that of a hydroxyethyl sulfonate salt. These salts are represented by the formula (II)

wherein X is a cation selected from the group consisting of sodium, potassium, ammonium and triethanolammonium ions.

In personal care compositions the amounts of the hydroxyethyl sulfonate salt in may range from about 0.1 to about 10%, preferably from about 0.3 to about 7%, and optimally from about 0.5 to about 5% by weight of the personal care composition. Most preferred among the hydroxyethyl sulfonate salts is sodium hydroxyethyl sulfonate.

Advantageously the pH of compositions of this invention may range from about pH 5.5 to 8, preferably from 6 to 7.8, and optimally from 6.8 to 7.8.

Personal care compositions containing the preservative system of this invention ordinarily will also contain water. These compositions may include a hydrophobic phase thereby forming an emulsion. Water-in-oil and oil-in-water as well as triplex emulsions may be useful as carriers according to the present invention. Amounts of water may range from about 10% to about 99%, preferably from about 30 to about 90%, and optimally from about 50 to about 70% water by weight of the composition.

Personal care compositions are products that include, but are not limited to, shampoos, bodywash, liquid and bar type hand cleansers, toothpastes, face and body lotions and skin creams. Common to most of these products are surfactant systems. Indeed, surfactant systems that foam (i.e. cleansing formulations) are particularly prone to microbial contamination because of high water content in these formulations. Preservative systems of this invention are therefore especially useful for cleansing formulations.

Consequently, compositions of this invention will include a surfactant. Amounts of the surfactant may range from about 0.1 to about 30%, preferably from about 1 to about 20%, and optimally from about 5 to about 15% by weight of the personal care composition.

The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) and trialkylamine oxides are also suitable nonionic surfactants.

Preferred anionic surfactants include salts of the following: fatty acids (i.e. soap), alkyl ether sulfates and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, $C_8$-$C_{20}$ sarcosinates, $C_8$-$C_{20}$ acyl lactylates, sulfoacetates and combinations thereof. Most preferred is sodium cocoyl isethionate.

Useful amphoteric surfactants include cocoamidopropyl betaine, $C_{12}$-$C_{20}$ trialkyl betaines, sodium lauroamphoacetate, and sodium laurodiamphoacetate.

Humectants may be present in the personal care compositions. These are generally polyhydric alcohol-type materials. Typical polyhydric alcohols include glycerin, propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from about 0.2 to about 40%, preferably between 1 and 25%, most preferably between 2 and 15% by weight of the composition. Most preferred is glycerin as an humectant or moisturizer.

Emollient materials may be formulated into the compositions. These may be natural or synthetic esters and hydrocarbons. Amounts of the emollients may range anywhere from about 0.1 to about 20%, preferably between about 1 and about 10% by weight of the composition.

Among the ester emollients are:

(a) Alkyl esters of saturated fatty acids having 10 to 24 carbon atoms. Examples thereof include behenyl neopentanoate, isononyl isonanonoate, isopropyl myristate and octyl stearate.

(b) Ether-esters such as fatty acid esters of ethoxylated saturated fatty alcohols.

(c) Polyhydric alcohol esters. Ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.

(d) Wax esters such as beeswax, spermaceti wax and tribehenin wax.

(e) Sugar ester of fatty acids such as sucrose polybehenate and sucrose polycottonseedate.

Natural ester emollients principally are based upon mono-, di- and tri-glycerides. Representative glycerides include cottonseed oil, borage oil, borage seed oil, primrose oil, castor and hydrogenated castor oils, rice bran oil, soybean oil, olive oil, safflower oil, shea butter, jojoba oil and combinations thereof. Animal derived emollients are represented by lanolin oil and lanolin derivatives. Amounts of the natural esters may range from about 0.1 to about 20% by weight of the compositions.

Hydrocarbons suitable for the compositions include petrolatum, mineral oil, $C_{11}$-$C_{13}$ isoparaffins, polybutenes, and especially isohexadecane, available commercially as Permethyl 101A from Presperse Inc.

Fatty acids having from 10 to 30 carbon atoms may also be suitable as components. Illustrative of this category are pelargonic, lauric, myristic, palmitic, stearic, isostearic, oleic, linoleic, linolenic and behenic acids.

Sunscreen agents may also be included in compositions of the present invention. Particularly preferred are such materials as ethylhexyl p-methoxycinnamate, available as Parsol MCX®, Avobenzene available as Parsol 17890, and benzophenone-3 also known as Oxybenzone. Inorganic sunscreen actives may be employed such as microfine (1 to 100 nm) titanium dioxide and zinc oxide. Amounts of the sunscreen agents when present may generally range from 0.1 to 30%, preferably from 2 to 20%, optimally from 4 to 10% by weight of the composition.

Structurants for aqueous compositions may be selected from inorganic water structurants, charged polymeric water structurants, water soluble polymeric structurants, associative water structurants, and mixtures thereof. Non-limiting examples of inorganic water structurants include silicas, polymeric gellants such as polyacrylates, polyacrylamides, starches, modified starches, crosslinked polymeric gellants, copolymers, and mixtures thereof. Non-limiting examples of charged polymeric water structurants include Acrylates/Vinyl Isodecanoate Crosspolymer, Acrylates/C10-30 Alkyl Acrylate Crosspolymer, Carbomers, Ammonium Acryloyldimethyltaurate/VP Copolymer, Ammonium Acryloyidimethyltaurate/Beheneth-25 Methacrylate Crosspolymer, Acrylates/Ceteth-20 Itaconate Copolymer, Polyacrylamide, and mixtures thereof. Non-limiting examples of water soluble polymeric structurants include cellulose gums and starches. Non-limiting examples of associative water structurants include xanthum gum, gellum gum, pectins, alginates such as propylene glycol alginate, and mixtures thereof.

Cationic deposition polymers may also be utilized. Non-limiting examples include polysaccharide polymers, such as cationic cellulose derivatives. Preferred are the salts of hydroxyethyl cellulose reacted with trimethyl ammonium substituted epoxide, referred to the industry as polyquarternium T10 which are available from Amerchol Corp. in their Polymer KG, JR and LR series of polymers.

Toothpastes formulated according to the present invention will generally contain a fluoride source to prevent dental caries. Typical anti-caries actives include sodium fluoride, stannous fluoride and sodium monofluoro phosphate. Amounts of these materials will be determined by the amount of fluoride releasable which should range between about 500 to about 1800 ppm of the composition. Other components of dentifrices can include desensitizing agents such as potassium nitrate and strontium nitrate, sweeteners such as sodium saccharine, aspartame, sucralose, and potassium acesulfam. Thickeners, opacifying agents, abrasives and colorants will normally also be present.

Colorants, opacifiers and abrasives may also be included in compositions of the present invention. Each of these substances may range from about 0.05 to about 5%, preferably between 0.1 and 3% by weight of the composition.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

Example 1

Experiments were conducted to evaluate antimicrobial activity against *Pseudomonas aeruginosa* of aqueous formulas containing sodium hydroxyethyl sulfonate, sodium cocoyl glycinate and combinations of these two materials. Samples were prepared at room temperature by mixing together sodium cocoyl glycinate and/or sodium hydroxyethyl sulfonate and water. The pH was adjusted by addition of aqueous hydrochloric acid to reach a 7.6 value. Amounts of each of the active components was 5%.

Test Method:

Challenge Test for the Evaluation of Preservative Capacity of Liquid Detergent and Personal Products Test Microorganism:

*Pseudomonas aeruginosa* ATCC 9027 obtained from American Type Culture Collection, Manassas, Va. 20108.

Procedure:

20 grams of product were inoculated with 0.2 ml of the microorganism at a level of 1.06E+07 or Log 7. A single inoculation was performed. At 2 day, 7 day, 14 day and 21 day time points after inoculation a 1 gram sample was aseptically removed into a neutralizing fluid (TAT Broth) and plated using Letheen Agar. The plates were incubated at 30° C. for 7 days. At the end of the incubation time the plates were removed and examined for microbial growth.

Calculation of Log Reduction:

The microorganisms recovered were converted into $Log_{10}$ and compared to initial inoculum count which then determined the Log Reduction. Logarithmic functions are the inverse of exponential functions. Log reduction was determined by the initial inoculum count minus the counts at each sampling time point.

TABLE I

| Component | Log Reduction Value | | | |
|---|---|---|---|---|
| | 2 day | 7 day | 14 day | 21 day |
| Sodium Cocoyl Glycinate | 1.1 | 1.1 | 0.8 | 0.2 |
| Sodium Hydroxyethyl Sulfonate | 1.1 | 0.9 | 0.8 | 0.5 |
| Sodium Cocoyl Glycinate and Sodium Hydroxyethyl Sulfonate (1:1) | 5.6 | 3.3 | 1.1 | 1.1 |

Based on the results recorded in the Table, it is seen that salt combinations of glycinate and hydroxyethyl sulfonate provide a strong immediate kill within 48 hours. The Log Reduction value for the 2 day application was 5.6. This value is known to be effective for commercial personal care compositions.

Examples 2-4

A series of shower gel formulas suitable for the present invention are recorded in Table II below.

TABLE II

| Ingredients | Example (wt %) | | |
|---|---|---|---|
| | 2 | 3 | 4 |
| Ammonium Laureth-3 Sulfate | 3.0 | 3.0 | 3.0 |
| Sodium Lauroamphoacetate | 16.7 | 16.7 | 16.7 |
| Sodium Cocoyl Glycinate | 10.0 | 8.0 | 6.5 |
| Lauric Acid | 0.9 | 0.9 | 0.9 |
| Trihydroxystearin | 2.0 | 2.0 | 2.0 |
| Guar Hydroxypropyltrimonium Chloride | 0.17 | 0.75 | 0.75 |
| Polyquaterium 10 | 0.45 | — | — |
| Polymethacrylamidopropyltrimonium Chloride | — | 0.24 | — |
| Polyquaternium-39 | — | 0.81 | — |
| PEG 90 M | 0.25 | — | — |
| PEG-14M | 0.45 | 2.45 | 2.45 |
| Linoleamidopropyl PG-Dimonium Chloride | — | 1.0 | 4.0 |
| Glycerin | 1.4 | 4.9 | 4.9 |
| Sodium Chloride | 0.3 | 0.3 | 0.3 |
| Sodium Benzoate | 0.25 | 0.25 | 0.25 |
| Disodium EDTA | 0.13 | 0.13 | 0.13 |
| Sodium Hydroxyethyl Sulfonate | 1.0 | 0.5 | 0.1 |
| Glydant ® DMDM Hydantoin ® | 0.37 | 0.37 | 0.37 |
| Citric Acid | 1.6 | 0.95 | 0.95 |
| Water | Balance | Balance | Balance |

Example 5

A shampoo composition useful in the context of the present invention is described in Table III below.

TABLE III

| Ingredient | Weight % |
|---|---|
| Ammonium Laureth Sulfate | 12.00 |
| Ammonium Lauryl Sulfate | 2.00 |
| Cocoamidopropyl Betaine | 2.00 |
| Sodium Cocoyl Glycinate | 5.00 |
| Sodium Hydroxyethyl Sulfonate | 0.50 |
| Glycerin | 5.00 |
| Dihydroxypropyltrimonium Chloride | 5.50 |
| Ethylene Glycol Distearate | 1.50 |

TABLE III-continued

| Ingredient | Weight % |
| --- | --- |
| Cocomonoethanolamide | 0.80 |
| Cetyl Alcohol | 0.60 |
| Polyquaternium-10 | 0.50 |
| Dimethicone | 1.00 |
| Sodium Citrate | 0.40 |
| Citric Acid | 0.39 |
| Sodium Xylene Sulfonate | 1.00 |
| Fragrance | 0.40 |
| Sodium Benzoate | 0.25 |
| Kathon CG ® Biocide | 0.0008 |
| Benzyl Alcohol | 0.0225 |
| Water | Balance |

Example 6

An aerosol packaged foaming cleanser useful in the context of the present invention is described in Table IV.

TABLE IV

| Ingredient | Weight % |
| --- | --- |
| Sodium Cocoyl Glycinate | 10.00 |
| Glycerin | 10.00 |
| Maleated Soybean Oil | 5.00 |
| Silicone Urethane | 1.00 |
| Polyglycero-4 Oleate | 1.00 |
| Sodium C14-16 Olefin Sulfonate | 15.00 |
| Sodium Lauryl Ether Sulphate (25% Active) | 15.00 |
| Cocoamidopropylbetaine | 15.00 |
| DC 1784 ® (Silicone Emulsion 50%) | 5.00 |
| Polyquaternium-11 | 1.00 |
| Sodium Hydroxyethyl Sulfonate | 1.00 |
| Water | Balance |

Example 7

A toilet bar illustrative of the present invention is outlined under Table V.

TABLE V

| Ingredient | Weight % |
| --- | --- |
| Sodium Soap (85/15 Tallow/Coconut) | 67.77 |
| Sodium Cocoyl Glycinate | 5.00 |
| Sodium Hydroxyethyl Sulfonate | 0.10 |
| Dimethicone | 2.00 |
| Sodium Chloride | 0.77 |
| Titanium Dioxide | 0.40 |
| Fragrance | 1.50 |
| Disodium EDTA | 0.02 |
| Sodium Etidronate | 0.02 |
| Fluorescer | 0.024 |
| Water | Balance |

Example 8

A foaming toothpaste according to the present invention can be formulated with the ingredients listed under Table VI.

TABLE VI

| Ingredient | Weight % |
| --- | --- |
| Zeodent ® 115 ® Silica | 20.00 |

TABLE VI-continued

| Ingredient | Weight % |
| --- | --- |
| Glycerin | 18.00 |
| Xanthan Gum | 7.00 |
| Sodium Carboxymethyl Cellulose | 0.50 |
| Sodium Bicarbonate | 2.50 |
| Sodium Hydroxyethyl Sulfonate | 2.00 |
| Sodium Cocoyl Glycinate | 1.50 |
| Sodium Fluoride | 1.10 |
| Sodium Saccharin | 0.40 |
| Titanium Dioxide | 1.00 |
| Pluronic ® F-127 ® Polyoxyalkylene Ether | 2.00 |
| FD&C Blue No. 1 | 3.30 |
| Menthol | 0.80 |
| PEG-10 Dimethicone | 0.50 |
| Water | Balance |

The foregoing description illustrates selected embodiments of the present invention. In light thereof, variations and modifications will be suggested to one skilled in the art, all of which are within the spirit and purview of this invention.

What is claimed is:

1. A preservative system comprising:
   (i) a cocoyl glycinate salt selected from the group consisting of sodium, potassium, ammonium and triethanolammonium cocoyl glycinate; and
   (ii) a salt of hydroxyethyl sulfonate of formula (II)

$$HOCH_2CH_2SO_3X \qquad (II)$$

wherein X is a cation selected from the group consisting of sodium, potassium, ammonium and triethanolammonium ions.

2. The system according to claim 1 wherein the glycinate salt is sodium cocoyl glycinate.

3. The system according to claim 1 wherein the hydroxyethyl sulfonate salt is sodium hydroxyethyl sulfonate.

4. The system according to claim 1 having a Log Reduction against *Pseudomonas aeruginsa* of at least 3.5 within 48 hours of application to an aqueous system.

5. The system according to claim 1 having a Log Reduction against *Pseudomonas aeruginsa* of at least 5 within 48 hours of application to an aqueous system.

6. A personal care composition comprising:
   (i) from about 0.1 to about 20% of a glycinate salt selected from the group consisting of sodium, potassium, ammonium and triethanolammonium cocoyl glycinate;
   (ii) from about 0.1 to about 10% of a salt of hydroxyethyl sulfonate of formula (II)

$$HOCH_2CH_2SO_3X \qquad (II)$$

wherein X is a cation selected from the group consisting of sodium, potassium, ammonium and triethanolammonium ions; and
   (iii) water.

7. The composition according to claim 6 wherein the glycinate salt is sodium cocoyl glycinate.

8. The composition according to claim 6 wherein the hydroxyethyl sulfonate salt is sodium hydroxyethyl sulfonate.

9. The composition according to claim 6 further comprising from about 0.1 to about 30% of a surfactant.

10. The composition according to claim 9 wherein the surfactant is sodium cocoyl isethionate.

* * * * *